US005742700A

United States Patent [19]
Yoon et al.

[11] Patent Number: 5,742,700
[45] Date of Patent: Apr. 21, 1998

[54] QUANTITATIVE DENTAL CARIES DETECTION SYSTEM AND METHOD

[75] Inventors: Douglas C. Yoon, Beverly Hills; Gregg D. Wilensky, Venice; Joseph A. Neuhaus, Marina del Ray; Narbik Manukian, Glendale; David C. Gakenheimer, Redondo Beach, all of Calif.

[73] Assignee: Logicon, Inc., Torrance, Calif.

[21] Appl. No.: 542,674

[22] Filed: Oct. 13, 1995

Related U.S. Application Data

[63] Continuation-in-part of Ser. No. 513,472, Aug. 10, 1995, abandoned.

[51] Int. Cl.$^6$ ........................................... G06K 9/00
[52] U.S. Cl. ................................. 382/132; 382/190
[58] Field of Search ........................... 382/128, 129, 382/130, 131, 132, 133, 134, 155, 156, 157, 158, 159, 160, 170, 172, 173, 181, 190, 209, 224, 254, 266, 270, 276, 278, 279, 280, 286, 308; 348/77, 66; 128/653.1; 378/38, 98, 116, 92, 98.8; 433/25; 364/413.02, 413.13, 413.01; 250/370.11, 368; 395/11, 22

[56] References Cited

U.S. PATENT DOCUMENTS

| | | | |
|---|---|---|---|
| 4,553,254 | 11/1985 | Bach et al. | 378/98 |
| 4,829,548 | 5/1989 | Halm et al. | 378/38 |
| 5,018,173 | 5/1991 | Komal et al. | 378/4 |
| 5,018,177 | 5/1991 | McDavid et al. | 378/62 |
| 5,101,421 | 3/1992 | Nishiki | 378/99 |
| 5,177,775 | 1/1993 | Onodera et al. | 378/99 |
| 5,179,579 | 1/1993 | Dove et al. | 378/38 |
| 5,195,114 | 3/1993 | Sairenji et al. | 378/40 |
| 5,214,686 | 5/1993 | Webber | 378/38 |
| 5,216,250 | 6/1993 | Pellegrino et al. | 250/370.09 |
| 5,224,140 | 6/1993 | Virta et al. | 378/38 |
| 5,260,871 | 11/1993 | Goldberg | 364/413.02 |
| 5,315,631 | 5/1994 | Hillen et al. | 378/98.8 |
| 5,331,166 | 7/1994 | Yamamoto et al. | 250/370.11 |
| 5,331,550 | 7/1994 | Stafford et al. | 364/413.02 |

OTHER PUBLICATIONS

Ecenbarger, William; "How Honest are Dentists?"; Reader's Digest; Feb. 1997; pp. 50–56.

Pitts, N.B.; "Detection of Approximal Radiolucencies in Enamel: A Preliminary Comparison Between Experienced Clinicians & An Image Analysis Method"; JADA, 1987, pp. 191–197.

Pitts, N.B., *Detection and Measurement of Approximal Radiolucencies by Computer Aided Image Analysis of Bitewing Radiographs*, Oral Surgery 58:358–366(1984).

Pitts, N.B. and Renson, C.E., *Further Development of a Computer–Aided Analysis Method of Quantifying Radiolucencies in Approximal Enamel*, Caries Res. 20:361–370(1986).

Pitts, N.B., *Monitoring The Behavior of Posterior Approximal Carious Lesions by Image Analysis of Serial Standardized Bitewing Radiographs*, British Dental Journal 162 (1987).

Pitts, N.B. and Renson, C.E., *Image Analysis of Bitewing Radiographs: A Histologically Validated Comparison with Visual Assessments of Radiolucency Depth in Enamel*, British Dental Journal 160:205–209 (1986).

(List continued on next page.)

*Primary Examiner*—Leo Boudreau
*Assistant Examiner*—Bijan Tadayon
*Attorney, Agent, or Firm*—Oppenheimer Poms Smith

[57] ABSTRACT

A caries detection system and method for quantifying a probability of lesions existing in tissues are presented. Digital X-ray images are segmented and further processed to generate feature statistics inputs for a neural network. The feature statistics include colinearity measurements of candidate lesions in different tissue segments. The neural network is trained by back propagation with an extensive data set of radiographs and histologic examinations and processes the statistics to determine the probability of lesions existing in the tissues.

18 Claims, 14 Drawing Sheets

OTHER PUBLICATIONS

Pitts, N.B. and Renson, C.E., *Reproducibility of Computer–Aide Image–Analysis–Derived Estimates of the Depth and Area of Radiolucencies in Approximal Enamel*, J. Dent. Res. 64:(10):1221–1224(1985).

Pitts, N.B., *Detection of Approximal Radiolucencies in Enamel: A Preliminary Comparison Between Experienced Clinicians and an Image Analysis Method*, J. Dent. Res. 15:191–197(1987).

Heaven, T.A., A.R. Firestone and F.F. Feagin, *Computer–based Image Analysis of Natural Approximal Caries on Radiographic Films*, J. Dent. Res. 71 (Special Issue):846–849(1992).

Heaven, T.A., R.A. Weems, A.R. Firestone, *The Use of a Computer–based Image Analysis Program for the Diagnosis of Approximal Caries from Bitewing Radiographs*, Caries Rels. 28:55–58(1994).

Duncan, R.C., et al., *Using Computers to Diagnose and Plan Treatment of Approximal Caries Detected in Radiographs*, JADA 126:873–882(1995).

Firestone, A.R., T.J. Heaven and R.A. Weems, *Computer–based System for Detecting Approximal Caries and Cavitation in Radiographic Images of Anterior Teeth*, Caries Res. 28: Abstract No. 37:191(1994).

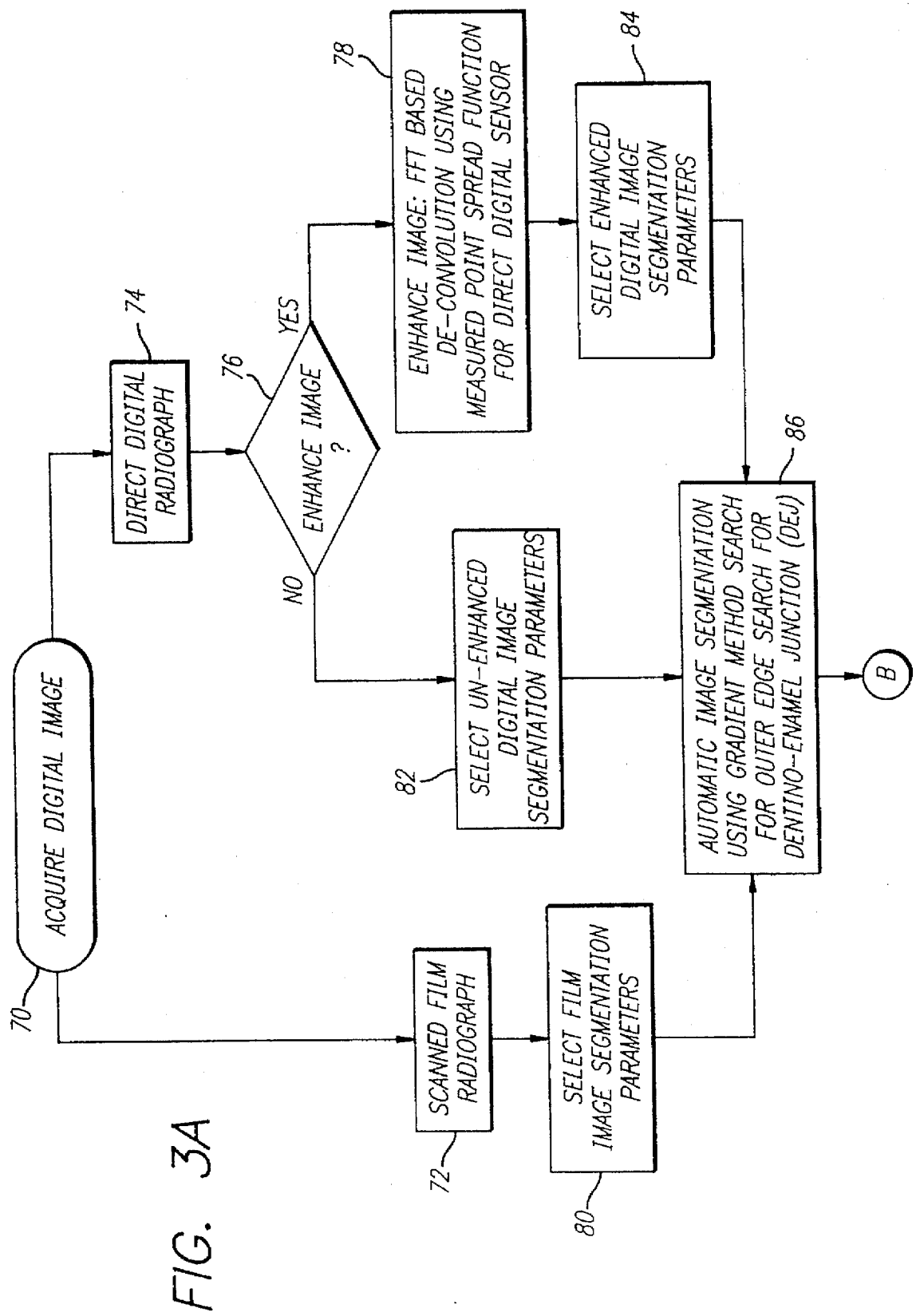

QUANTITATIVE DENTAL CARIES DETECTION SYSTEM AND METHOD

CROSS-REFERENCE TO RELATED APPLICATION

This application is a continuation-in-part of U.S. Pat. application Ser. No. 08/513,472, filed Aug. 10, 1995, now abandoned entitled QUANTITATIVE DENTAL CARIES DETECTION SYSTEM AND METHOD, by Douglas C. Yoon, et al.

BACKGROUND OF THE INVENTION

1. Field of the Invention

The present invention relates to a system and method for the digital detection of tissue lesions and, more particularly, pertains to a system and method for quantifying a probability of lesions existing in tissues.

2. Description of the Related Art

According to the *Journal of the American Dental Association*, Volume 108, May 1984, page 755, dentists fail to detect carious lesions in teeth a significant fraction of the time (up to 40%). Healthy teeth are misdiagnosed a significant fraction of the time as well (up to 20%). In part, this problem is due to the fact that dentists are unable to directly view carious lesions on proximal surfaces, i.e., between the teeth. The human eye is an imperfect tool for visually analyzing dental x-rays because of its tendency to smooth out intensity gradients. Furthermore, substantial variations in dental x-ray images are attributable to variations in film type, exposure level, tooth structure and shape, and location and extent of lesions.

Accordingly, an object of the present invention is to provide a tool for clinicians which reliably quantifies the probability of a lesion being present in tissues, an "electronic second opinion."

Another object is to provide a digital imaging method for quantifying a probability of lesions existing in tissues.

Another object is to provide a quantitative method which employs segmentation techniques to identify boundaries between adjacent tissues under analysis.

Another object is to provide a quantitative method which extracts and derives statistics from digital imagery in consideration of segmentation boundaries.

Another object is to provide a quantitative method wherein neural network techniques are applied to analyze feature statistics derived from digital images of tissues to detect and classify lesions within the tissues.

Another object is to develop a data base of lesions in relevant tissues and to optimally employ such a data base for training a neural network.

SUMMARY OF THE INVENTION

In accordance with a specific illustrative embodiment of the present invention, a method for quantifying a probability of lesions existing in tissues includes the steps of: processing an image of at least two adjacent tissues to establish segments of the image; processing portions of the image within each segment to identify features within the tissues; processing the image to generate values for parameters (hereinafter "feature statistics") pertaining to the features; and processing the feature statistics to determine probabilities of the identified features being lesions.

In a broader aspect of the present invention, a method for quantifying a probability of lesions existing in tissues includes the steps of: providing feature information for image segments corresponding to at least two adjacent tissues; and processing the feature information to generate feature statistics for subsequent processing by a neural network.

In a further aspect of the present invention, a system for the digital detection of dental lesions includes a source of digitized x-ray images of teeth, a processor, and a display. The images have variable intensities which are analyzed to identify outer surfaces and interfaces of the imaged teeth. The processor employs the identified outer surface and interface to identify significant changes in intensity along successive space lines extending generally parallel to the tooth surface and generally parallel to the interface between the enamel and the dentine. The processor is additionally programmed to compare the variations in intensity with stored data relating to known dental lesions or caries and determined by such comparison the probability of such lesions being present. The display provides visible indicia corresponding to the locations of probable lesions.

DESCRIPTION OF THE DRAWINGS

Other objects, features and advantages of the invention will become readily apparent upon reference to the following detailed description when considered in conjunction with the accompanying drawings, in which like reference numerals designate like parts throughout the figures thereof, and wherein:

FIG. 3A is a flowchart of an automatic image segmentation aspect of a method of the present invention;

DETAILED DESCRIPTION OF THE PREFERRED EMBODIMENTS

Figure 1:
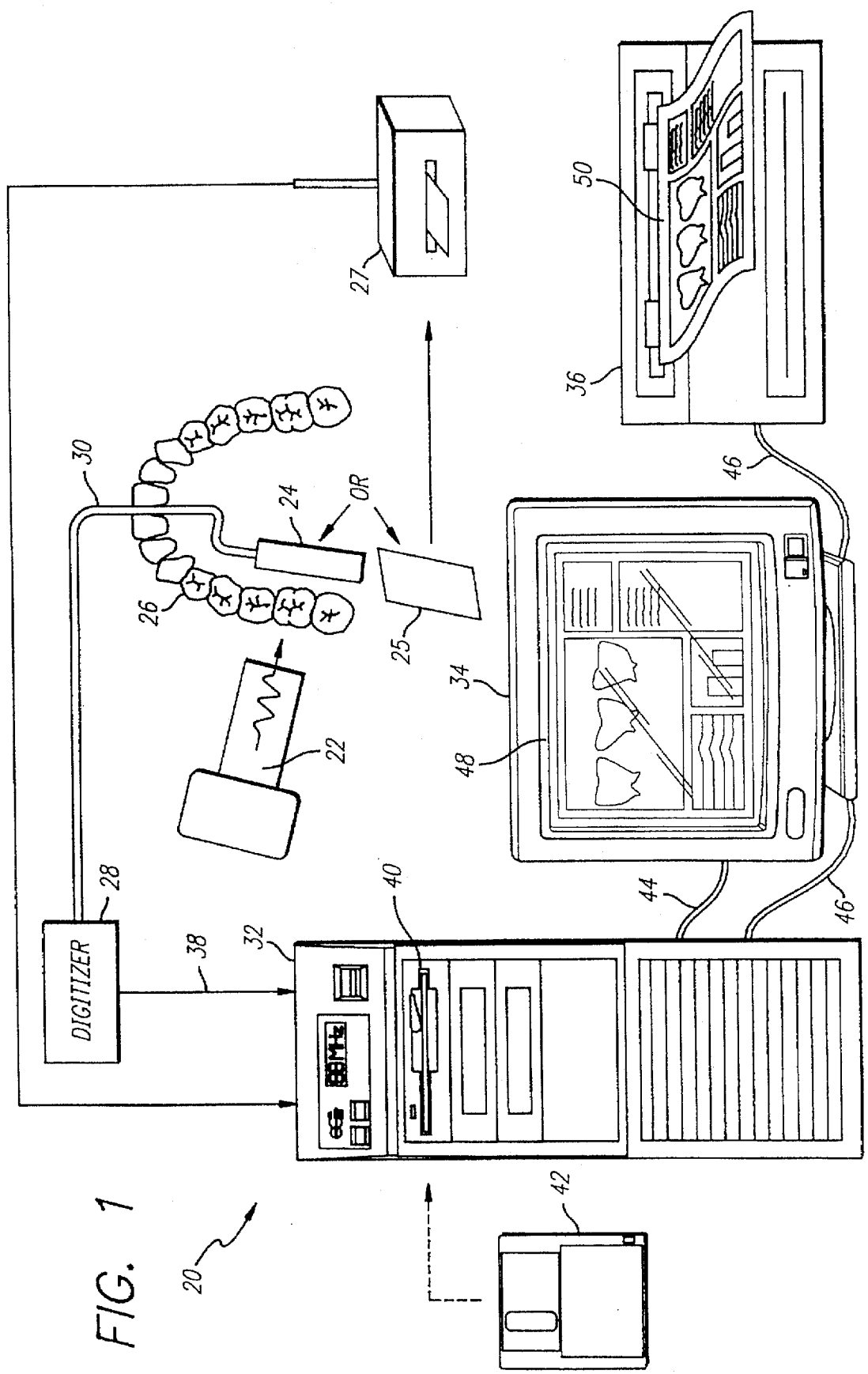
FIG. 1 is a perspective view of the quantitative dental caries detection system of the present invention.

FIG. 1 is a perspective view of a quantitative dental caries detection system 20 according to the present invention. An x-ray source 22 and an x-ray sensor 24 are employed to produce two dimensional x-ray images of teeth 26. The x-ray sensor 24 may comprise a charge coupled device (CCD) x-ray sensor. A digitizer 28 receives the analog output of the CCD and converts it to a digital format for receipt by a computer 32. The sensor 24 should provide at least 8–10 line pairs/mm resolution. The detection system 20 additionally includes a computer 32, a monitor 34 and a printer 36. Digitized x-ray image information is provided from the digitizer 28 to the computer 32, for example, via an interface cable 38. Alternately, an x-ray film image may be input to the computer 32 by scanning and digitizing a film radiograph 25 with a commercially available film scanner 27 such as the Nikon Coolscan system. The computer 32 includes memory devices as well as a disk drive 40. A storage device such as diskette 42 provides executable software to the computer 32. Many aspects of the quantitative method of the present invention may be embodied in the form of software which is stored on a memory device such as the diskette 42 and executed by a processor such as the computer 32. The detection system 20 additionally includes a monitor interface cable 44 which electrically connects the computer 32 and the monitor 34. A printer interface cable 46 similarly interconnects the computer 32 with the printer 36. The monitor 34 includes a display 48 and the printer 36 generates a corresponding printout 50.

Figure 2:
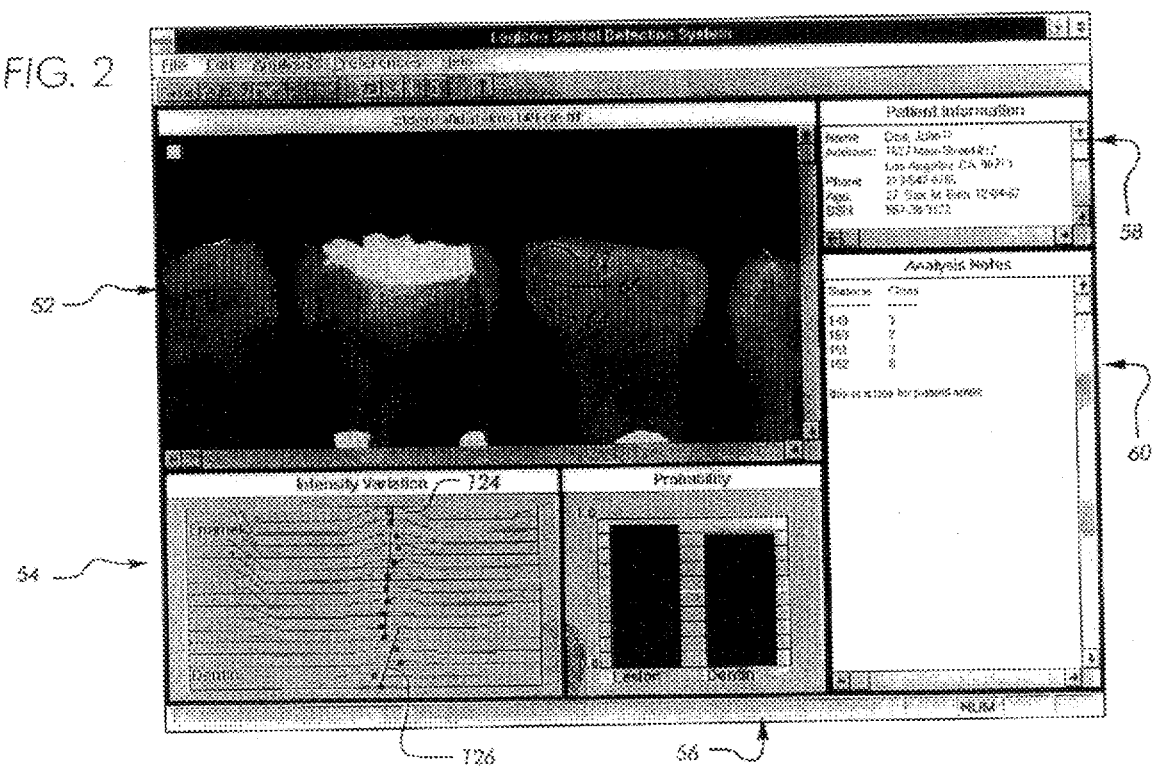
FIG. 2 is a photographic board of an enlarged front view of the display of FIG. 1.

FIG. 2 is an enlarged front view of the display 48 shown in FIG. 1. The display 48 is preferably partitioned into a plurality of display portions including a digitized image portion 52, an intensity variation plot 54, a probability graph 56, a patient information portion 58 and an analysis notes portion 60. Generally, the quantitative dental caries detection system 20 processes acquired digital images and identifies particular segments of these images by determining outer boundaries of teeth and the dentinoenamel junction (DEJ) 62. The detection system 20 processes the digitized images in consideration of the foregoing segmentation and employs trained network weights to quantify probabilities of lesions existing in the various segments of the radiographed teeth. As one of the outputs of the process, FIG. 2 shows a first lesion boundary 64 and a second lesion boundary 66 overlayed on the digitized image portion 52. The first lesion boundary 64 and the second lesion boundary 66 both extend, from left to right, from the outer boundary of the tooth's enamel through the dentinoenamel junction 62 and into the dentine of the tooth. The intensity variation plot 54 and the probability graph 56 will be explained in greater detail with reference to FIG. 4.

FIG. 3A is a flowchart of an automatic image segmentation aspect of the method of the present invention. Software resident within the computer 32 receives and processes the digitized image at 70. If the input image is a scanned film radiograph, such as one produced with a Nikon Coolscan film scanner, execution of the image segmentation algorithm is directed toward block 72. If the input image is a direct digital radiograph (as produced, for example, by equipment from Schick Technologies, Inc.) execution of the image segmentation algorithm is directed toward executable block 74. Image segmentation is automatically implemented using a gradient method to identify the outer boundaries of the teeth and their dentinoenamel junctions. A key feature of the invention is the employment of different sets of segmentation parameters in the segmentation algorithm which take into account the varying degrees of image sharpness or clarity as between scanned film radiographs, unenhanced direct digital radiographs, and enhanced direct digital videographs.

Figure 4:
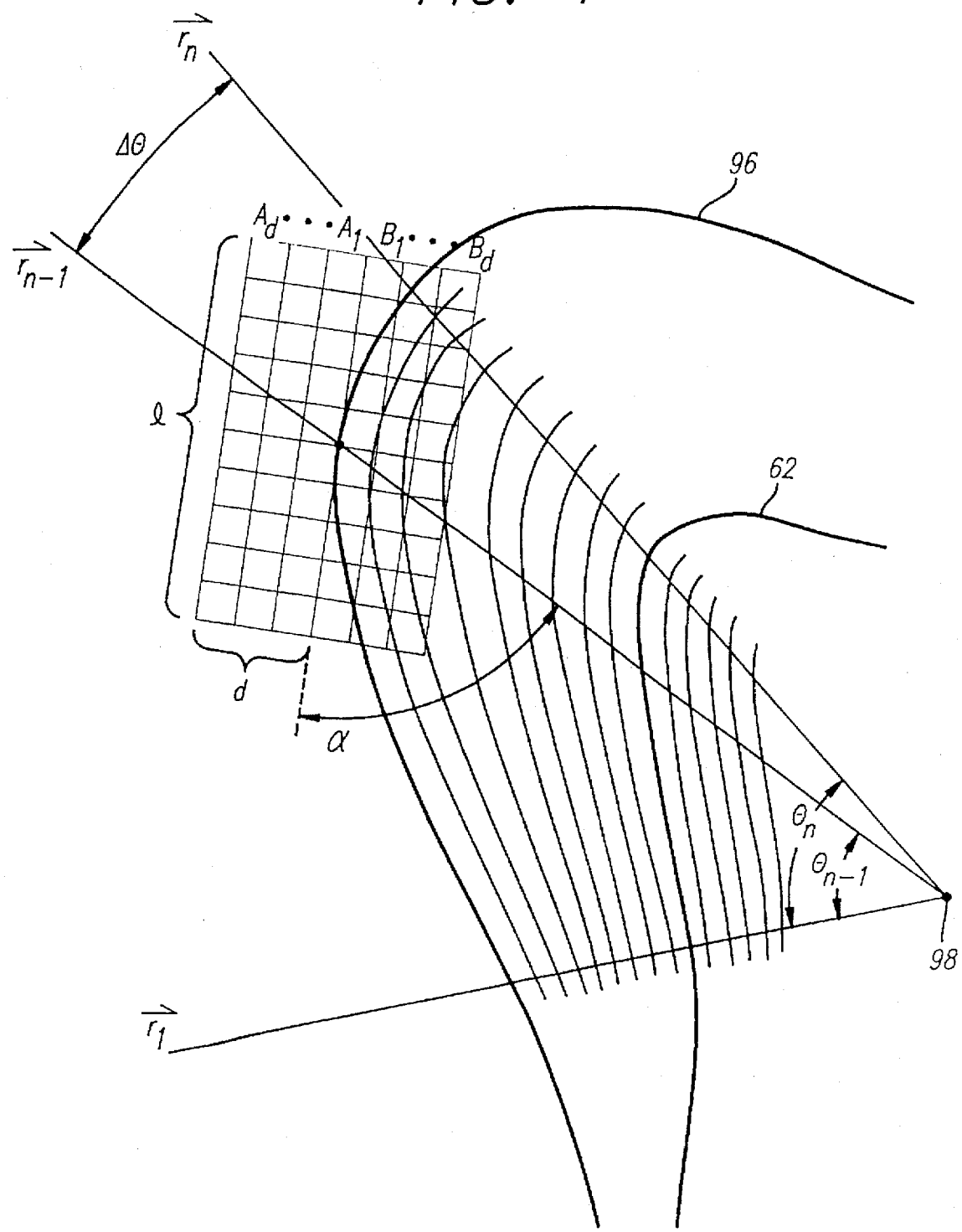
FIG. 4 illustrates digital image processing employing a gradient technique according to the present invention.

Tissue boundaries and junctions between adjacent tissues are preferably determined by image processing based on polar coordinates, exploiting the substantially radially symmetric structure of the tooth, as is best illustrated in FIG. 4. The gradient method of the present invention employs a "sliding" two dimensional matrix of pixel intensities comprising 1×2•d elements. Generally, the tissue boundaries and interfaces between tissues are found by identifying the maximum gradients along radial vectors $r_1, r_2, \cdots r_{n-1}, r_n$. The segmentation parameters mentioned above include:

l: The length of the gradient matrix of pixels intensities.

d: Half of the width of the gradient matrix of pixels intensities.

α: An angle defined by a vector along the length of the gradient matrix of pixel intensities and by the radial vector (a.k.a., matrix orientation angle).

ΔΘ: The angular difference between successive radial vectors.

Further with regard to FIG. 3A, decisional diamond 76 directs execution of the image segmentation algorithm depending upon whether a direct digital radiograph is to be image enhanced. If yes, a Fast Fourier Transform (FFT) based deconvolution using a laboratory measured point spread function is implemented at executable block 78. The foregoing deconvolution sharpens the direct digital radiograph and has been found to improve performance of the image segmentation algorithm.

As discussed above, the segmentation parameters vary depending upon the source of the digital image. Film image segmentation parameters are selected at executable block 80 if the source of the digital image is a scanned film radiograph. Unenhanced digital image segmentation parameters are selected at executable block 82 if the source of the digital image is an unenhanced direct digital radiograph. Enhanced digital image segmentation parameters are selected at executable block 84 if the source of the digital image is an enhanced direct digital radiograph. The segmentation parameters are varied to optimize the image segmentation algorithm for different digital image sources which are provided in varying degrees of image sharpness or clarity. At executable block 86, an automatic image segmentation algorithm using a gradient method processes the digital image in consideration of the segmentation parameters selected for that particular image. The following equation provides for the calculation of the gradient:

$$\text{gradient} \propto \sum_{i=1}^{d} A_i \omega_i - \sum_{i=1}^{d} B_i \omega_i,$$

where $A_i$ and $B_i$ are the sums of the pixel intensities along the $i^{th}$ strips (FIG. 4) and $107_i$ is a weight factor which, for example, may vary linearly from 1 to 0 as i varies from 1 to d. The location of the relevant tissue boundary is where the highest gradient is found. This search is performed over a user defined range of angles $\theta_i$ about a tooth centroid 98 (FIG. 4). In turn, for each $73_i$ a search is performed over a range of gradient matrix orientation angles $\alpha_i$ and in turn for each $\alpha_i$ search is performed along the corresponding radial vector to $r_i$ find $r_{max_i}$, which is the range along vector $r_i$ at which the gradient is maximized. $r_{max_i}$ and $\theta_i$ are the coordinates of points along the tissue boundary.

Further with regard to the segmentation parameters, the strip length (l), strip thickness (d) and matrix orientation angles ($\alpha_i$) are varied as necessary to accommodate differences in sharpness or clarity associated with the various sources of digital images. The matrix orientation angle ($\alpha_i$) is preferably varied between 60° and 120° at 10° increments or finer and the angle ($\Delta\Theta$) is preferably set at approximately 1°. The subject matter of the present invention additionally contemplates an image segmentation algorithm which automatically or adaptively adjusts the foregoing parameters during execution.

Figure 3B:
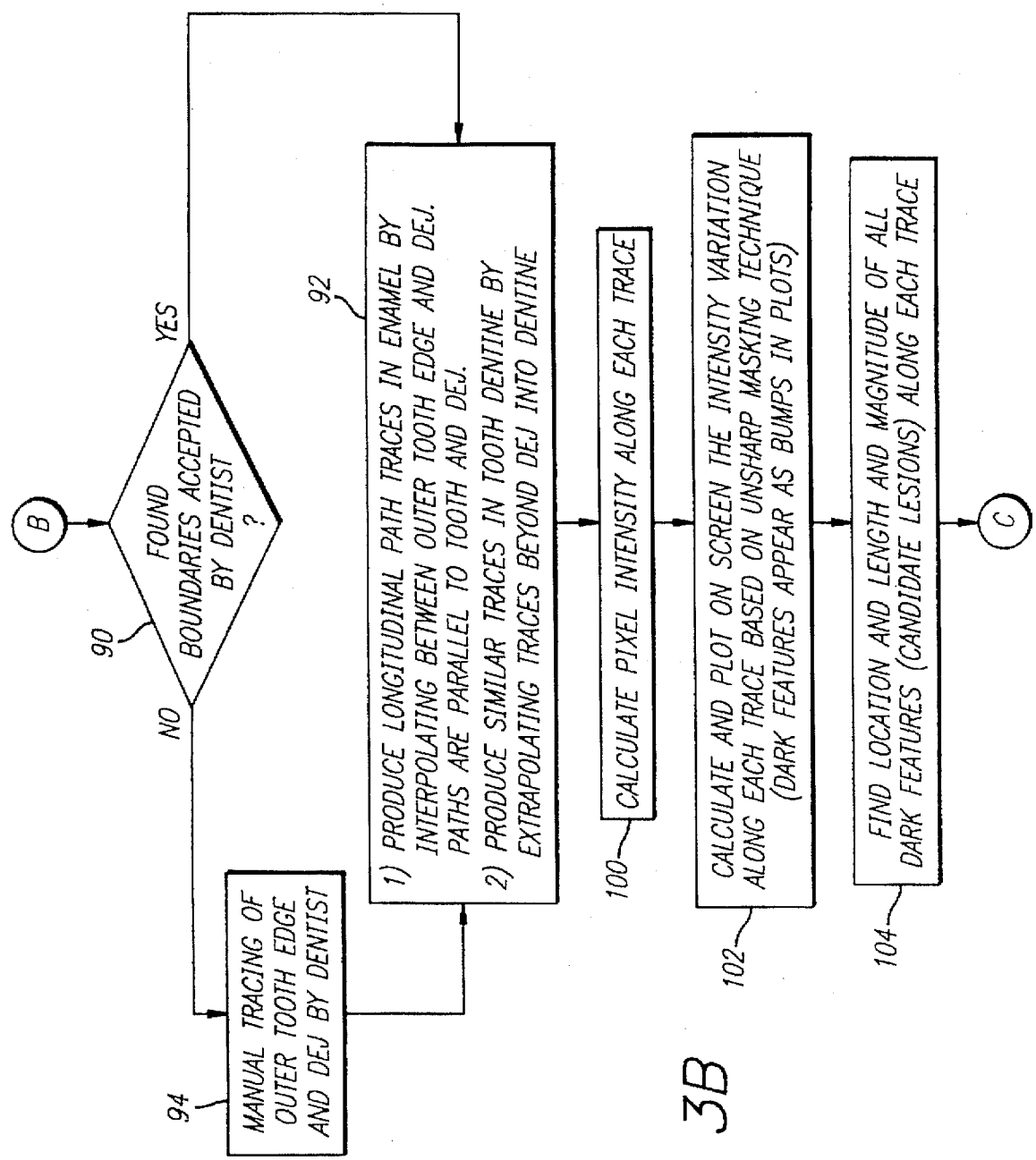
FIG. 3B is a flowchart of a feature extraction aspect of a method of the present invention.

FIG. 3B is a flowchart of a feature extraction aspect of the method of the present invention. Generally, the method of the present invention next employs the segmentation results to assist in the identification of candidate lesions within the subject tissue. In the case of teeth as the subject tissues, if the boundaries identified by the image segmentation algorithm are found at decisional diamond 90 to be acceptable to the dentist, the feature extraction algorithm advances to executable block 92. Otherwise, the dentist manually traces the outer boundaries of the tooth and the dentinoenamel junction at block 94. Generally, the system and method of the present invention address the problem of deriving coherent density features from intensity variation data. A preferred method partitions the radiograph (also commonly referred to as an "x-ray image") into portions depending upon the results of the image segmentation calculations. According to a preferred method and as illustrated in FIG. 4, the outer boundary 96 and the dentinoenamel junction 62 are then used to further partition the resulting enamel and dentine segments into substantially parallel strips or traces at successively deeper levels into the tooth which are later used for the feature extraction aspect of the present invention as discussed infra. In operation, a user selects a portion of the tooth by, for example, moving a screen cursor to a desired centroid 98 and clicking a user input device such as mouse. An angular range from $r_1$ to $r_1$ is similarly selected by movement of the mouse from the centroid 98 toward the tooth surfaces of interest.

Further with reference to FIG. 3B, pixel intensities I(x), where x represents the distance along the trace relative to the beginning of the trace, are calculated for a series of points along each trace at executable block 100. The feature extraction algorithm next calculates intensity variations V(x) along each trace based upon high pass filtering techniques. Such techniques correct for the effect of tooth geometry on the x-ray image and enhance the ability to identify local variations in intensity. A preferred digital high pass filter embodies the function $$V(x_i) = \frac{\sum_{j=-L}^{+L} I(x_{i+j})}{2L+1} - \frac{\sum_{k=-H}^{+N} I(x_{i+k})}{2H+1}$$

where L>H and where L and H represent distances in pixel units from $x_i$ along the traces. A broad length average is provided by calculating an intensity average for points between $x_{i-}L$ and $x_{i+}L$ along a trace. A narrow length average is provided by calculating an intensity average between $x_{i-}H$ and $x_{i+}H$ along a trace. The high pass filter function $V(x_i)$ represents the difference between the broad length average in intensity and the narrow length average in intensity at $x_i$. Appropriate scale factors may be employed in the foregoing equation to relate trace length units (which vary from trace to trace) to pixel units. It should additionally be understood that the foregoing equation is an approximation of a mathematical integral and that other filtering techniques may be employed.

As shown in FIG. 2, intensity variations along each trace may be plotted with dark features appearing as bumps in the plots. After the high pass filtering technique at executable block 102 is completed, all dark features (candidate lesions) along each trace are located and their lengths and magnitudes are determined at executable block 104. More generally, the segments are divided into families of traces within the outer boundary of the tooth. The families of traces are not necessarily oriented substantially parallel to the DEJ; appropriate coordinate transformation algorithms may be employed to compensate for particular orientations of the traces. It should be noted that the present invention additionally contemplates the application of alternative two-dimensional high pass filtering techniques, such as unsharp masking, wherein the segments are not necessarily divided into strips or traces. Although more computationally demanding, such an alternative two dimensional technique would be less sensitive to segmentation errors and, more specifically, to errors in the DEJ calculation.

Figure 3C:
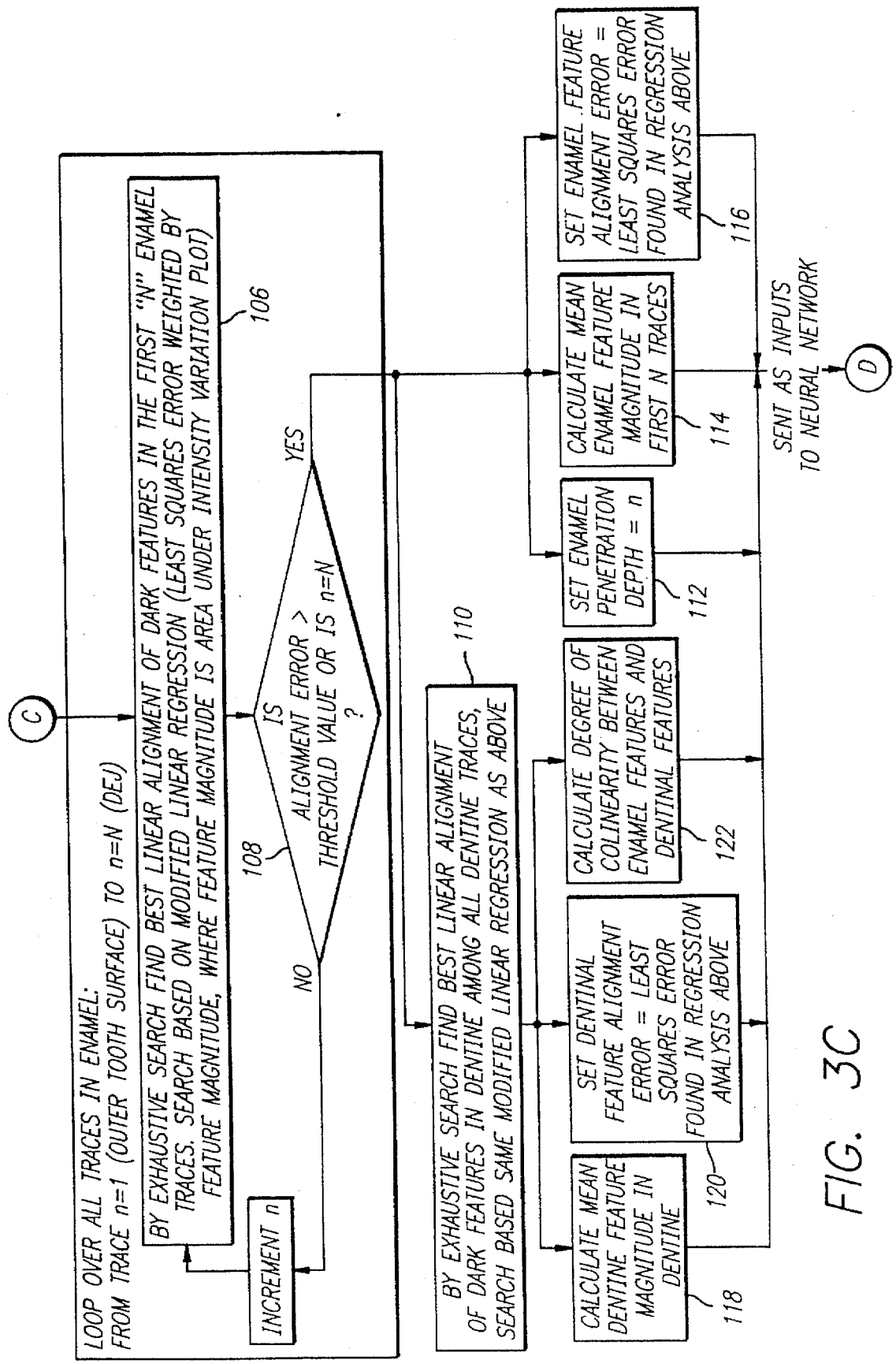
FIG. 3C is a flowchart of a feature statistics aspect of a method of the present invention.

FIG. 3C is a flowchart of a feature statistics aspect of the method of the present invention. The feature statistics algorithm generally functions to identify the best linear alignments of dark features in both the enamel and the dentine and to calculate the values of a limited number of parameters or inputs for subsequent processing, preferably by a neural network. The traces shown in FIG. 4 are again employed to search for the best linear alignment of dark features. The search is preferably based upon a linear regression using the size and location of features in each trace.

The alignment and depth of features are evaluated by two metrics, $\epsilon_s(N)$ and $A_s(N)$. $\epsilon_s(N)$ represents the scaled alignment error and As(N) represents the scaled mean feature magnitude. $\epsilon_s(N)$ and As(N) are associated with a candidate set of features from the first N traces, where one feature is selected from each trace. As will be described later, $\epsilon_s(N)$ is used to find the best linear alignment of features found in the trace and As(N) is used to determine the depth of penetration into the tooth of the features.

$\epsilon_s(N)$ and As(N) are calculated by first computing the best fit line through the candidate set of N features through standard linear regression. Also, the magnitude of the selected feature in each trace is computed (e.g., as the area under the bumps in the intensity variation plot 54 of FIG. 2). From these values the mean feature magnitude, A(N), is computed. Next, the RMS deviation associated with the position of the features ($x_{feature}$) and the best fit line ($x_{fit}$) through the features is computed as $$\epsilon(N) = \sqrt{\sum_{i=1}^{N} (x_{fit} - x_{feature})^2 / N}$$

Finally the scaled error which takes into account the mean magnitude of the features, is given by $$\epsilon_s(N) = \epsilon(N)(1 - \exp(-A(N)))$$

and the scaled magnitude is given by $$\overline{A}_s(N) = A(N)\, \epsilon_s(N).$$

The present invention additionally contemplates other techniques for scaling $\epsilon_s(N)$ and As(N) in consideration of the mutual biasing effect of these metrics upon each other. The area term As(N) is used to determine the end of a lesion. The error term $\epsilon_s(N)$ is used to determine the best alignment. Feature characterization is dependent upon the scaling of $\epsilon_s(N)$ and As(N). For example, weighting the area term by the error term helps prevent the selection of large but randomly positioned dark features as might occur in an image with large-scale mottling. Similarly, weighting the error by the mean area helps prevent the selection of small but aligned features as might occur by chance in a noisy image. The following discussion illustrates how the metrics $\epsilon_s(N)$ and As(N) are used to find the location and depth of a candidate lesion.

As shown in FIG. 4, the enamel segment includes a total of ten traces between and including the outer boundary 96 and the DEJ 62. The deeper the lesion penetrates into the tooth, the more processing is required to determine the best linear alignment by linear regression techniques. For example, if two candidate dark features are found in each of the outermost three traces, eight different calculations ($2^3$) are required for an exhaustive search to find the best fit within those three traces. As such, a key feature of the present invention is the development of a procedure for automatically stopping the calculations in the enamel segment after a determination is made that the lesion has ended. In a preferred embodiment of the feature statistics algorithm, a coherent feature is searched for in the first three traces starting at the outer boundary 96. When the best fit exhibiting the greatest degree of colinearity is identified by selecting the combination of features with the lowest scaled error, $\epsilon_s(N)$, this value and the associated scaled feature magnitude, As(N), are stored. Other information associated with this combination of features is also stored. As shown in FIG. 3C, executable block 106 is again implemented but now processes the intensity variation information for the first four traces. Similarly, the lowest scaled error, the scaled feature magnitude, and information associated with the combination of features are stored. With the addition of each trace to the calculation of executable block 106, a new scaled feature magnitude is calculated and compared against the immediately preceding calculation. When a decrease in successive scaled magnitudes exceeds a predetermined threshold value, the feature statistics algorithm at decisional diamond 108 redirects execution of the algorithm to executable block 110. When the threshold is exceeded, a sufficiently large decrease in the scaled magnitude (as compared to the previous scaled magnitude or, preferably, to a running average of all previous scaled magnitudes) has occurred indicating an end in the feature. If the threshold is not exceeded by the time n=N, this indicates that the feature has reached the DEJ and the algorithm proceeds to executable block 110.

A search for the best linear alignment of dark features in the dentine is preferably a simplified calculation comprising a single iteration wherein the intensities along the first five traces of the dentine are processed. Additionally, it has been found that there is little value to processing image traces greater than halfway through the dentine.

In a preferred embodiment of the present invention, only six parameters or feature statistics are provided as inputs to a neural network. FIG. 3C shows that the feature statistics algorithm assigns an enamel penetration depth at executable block 112. Additionally, a scaled mean enamel feature magnitude is calculated at executable block 114 in the traces between the outer boundary 96 and the trace corresponding to the enamel penetration depth as established at executable block 112. The scaled enamel feature alignment error as discussed above is also sent at executable block 116 to the neural network as an input.

Statistics pertaining to the dentine are also provided to the neural network. At executable block 118, the scaled mean dentine feature magnitude is calculated and provided to the neural network. A scaled dentinal feature alignment error from the foregoing regression analysis is also sent at executable block 120 to the neural network. Additionally, a degree of colinearity between enamel features and dentinal features is calculated and provided to the neural network at executable block 122. The degree of colinearity between enamel and dentinal features is conceptionally illustrated in the intensity variation plot 54 of FIG. 2 by the enamel linear regression line 124 and the dentine linear regression line 126. The degree of colinearity between enamel and dentinal features is calculated as the average distance, along each dentinal trace between line 126 and the projection of line 124 into the dentine.

Figure 3D:
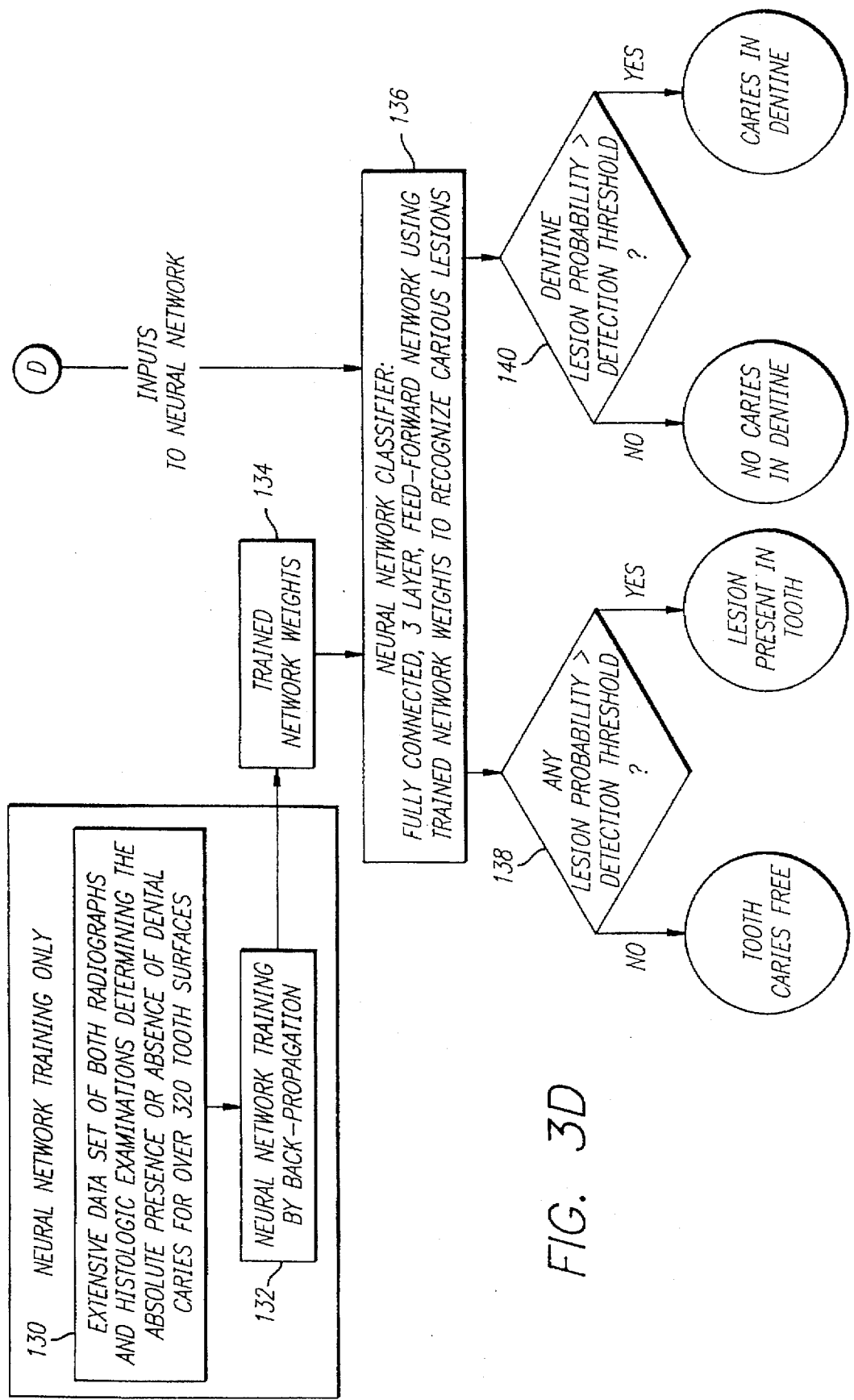
FIG. 3D is a flowchart of a classifier aspect of a method of the present invention.

FIG. 3D is a flowchart of a classifier aspect of the method of the present invention. In a preferred embodiment, a data base of laboratory exam inputs is assembled at block 130. Radiographic parameters include exposure levels, film speeds, digital sensor characteristics and tooth overlap geometries. An extensive data set is developed by cross sectional analysis of teeth used to determine the absolute extent of lesions. For example, 320 tooth surfaces are provided by four tooth types (incisor, canine, premolar, molar), four lesion depths (clean, >½ enamel, full enamel, >½ dentine) and 20 examples of each type and depth based on statistical analysis. A simplified classification or scoring system is set forth below:

0: clean tooth
1: lesions penetrating less than halfway into the enamel
2: lesions penetrating more than halfway into the enamel
3: lesions penetrating into dentine As shown in FIG. 3D, training of the neural network by back-propagation is effected at executable block 132. The resulting trained network weights at block 134 and the inputs from the feature statistics algorithm are provided to a neural network classifier 136. In a preferred embodiment, the neural network classifier 136 comprises a fully connected, three-layer, feed forward, network using trained network weights to recognize carious lesions. If the probability that any lesion exists exceeds a predetermined detection threshold, the system 20 indicates that a lesion is present in the tooth as shown in the probability graph 56 of FIG. 2. If decisional diamond 138 results in a negative determination, the system indicates that no suspicious features were found. The neural net is trained to generate the probability of a lesion being present in the selected region on the tooth. This probability (p) could be either the probability of any lesion or the probability of a lesion penetrating the dentine (distinct neural nets provide each probability). The probability (p) is calculated as shown below:

$$p = \sigma\left(\sum_{j=1}^{n\text{ hidden nodes}} W'_j \sigma\left(\sum_{i=1}^{N} W_{ji}X_i - V_j\right) - V'\right)$$

where:

$x_i = i^{th}$ input to neural net;

i=1, 2 ... N;

N=number of features;

$W'_j$, $W_{ji}$ are the network weights; $V'$, $V_j$ are the network thresholds; and $$\sigma(y) = \frac{1}{1 + \exp(-y)}$$

is the neural node transfer function
where (y) is the summation term within the brackets in the above probability equation.

The weights and thresholds are established by training on a database which is preferably extensive.

The classifier algorithms are structured as shown in FIG. 3D because it is vitally important for a dentist to treat a tooth which has lesions in its dentine. The detection threshold of decisional diamond 140 may be varied appropriately in view of the foregoing.

Figure 5:
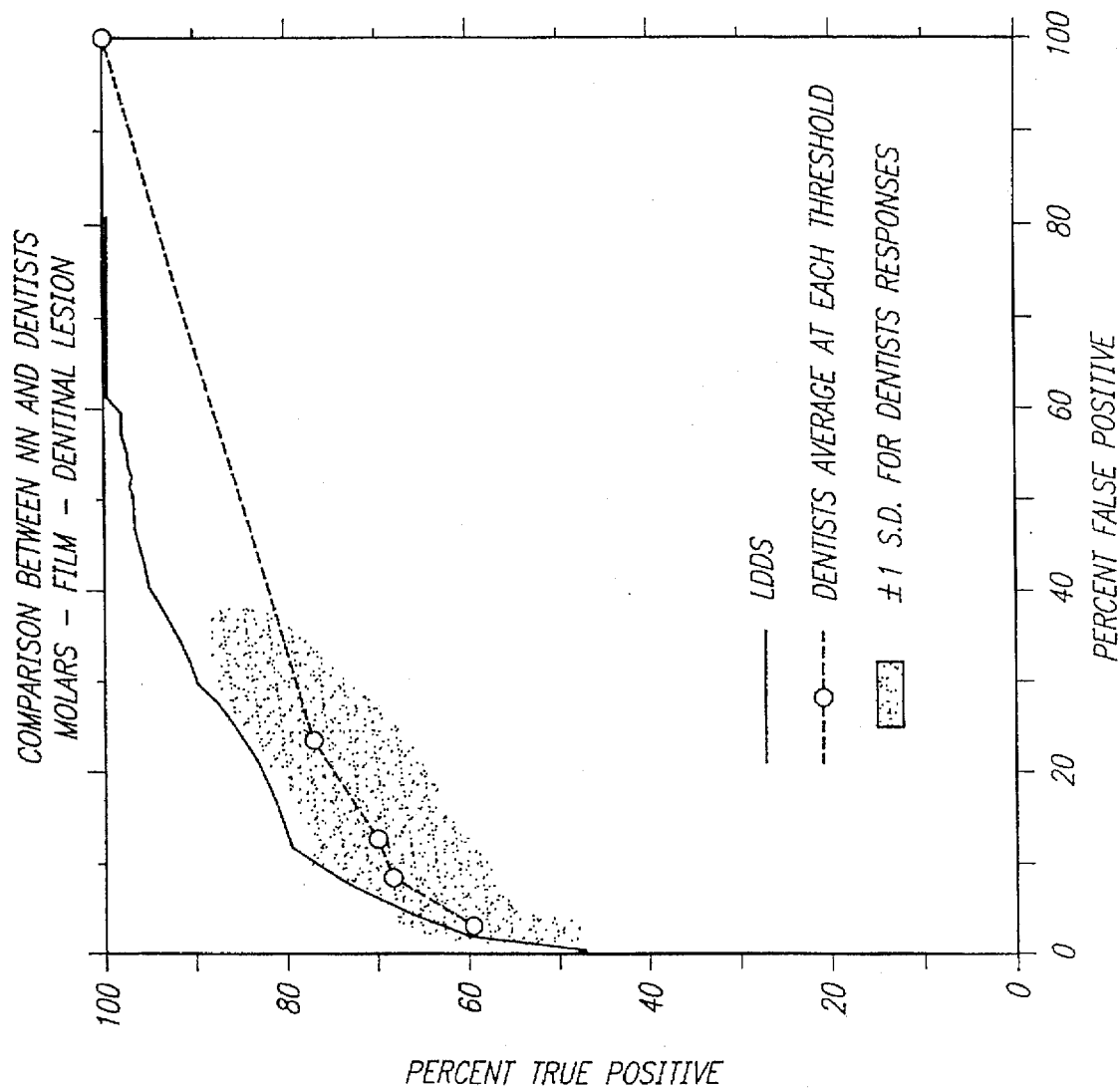
FIG. 5 compares the performance of the quantitative dental caries detection system for finding dentinal lesions in molars using film images with the performance of dentists and additionally illustrates by the shaded region plus and minus one standard deviation about the mean of the dentists' responses.

FIG. 5 compares the performance of the quantitative dental caries detection system 20 on film images of molars with the performance of dentists. The performance comparison was based on a set of radiographic images taken with standard film radiography (Kodak D film) and was determined by standard receiver operator characteristic (ROC) analysis. An ROC analysis measures the tradeoff between the false positive identification rate (in this case, the percentage of teeth free of caries in the dentine which are incorrectly classified as having a lesion in the dentine) versus the true positive identification rate (in this case, the percentage of teeth with a lesion in the dentine which are correctly identified). An ROC curve is generated by measuring the false positive and true positive rates for a range of detection confidence levels. The greater the area under the ROC curve, the better the overall performance. Observed data shows that the Logicon Dental Detection System (LDDS) exemplifying the present invention outperformed a team of eleven trained dentists in detecting interproximal lesions which have penetrated into the dentine in a test for four different categories of lesions on 80 surfaces.

FIG. 5 additionally illustrates plus and minus one standard deviation about mean of the dentists' responses. The shaded region represents the range encompassing approximately 68% (plus and minus one standard deviation about the mean) of the dentists' individual responses. The larger, hollow dots correspond to five decision thresholds along an average response trace for the tested dentists. In comparison, the LDDS outperforms the dentists' mean response as the majority of the individual responses for the dentists are below the LDDS curve.

Figure 6:
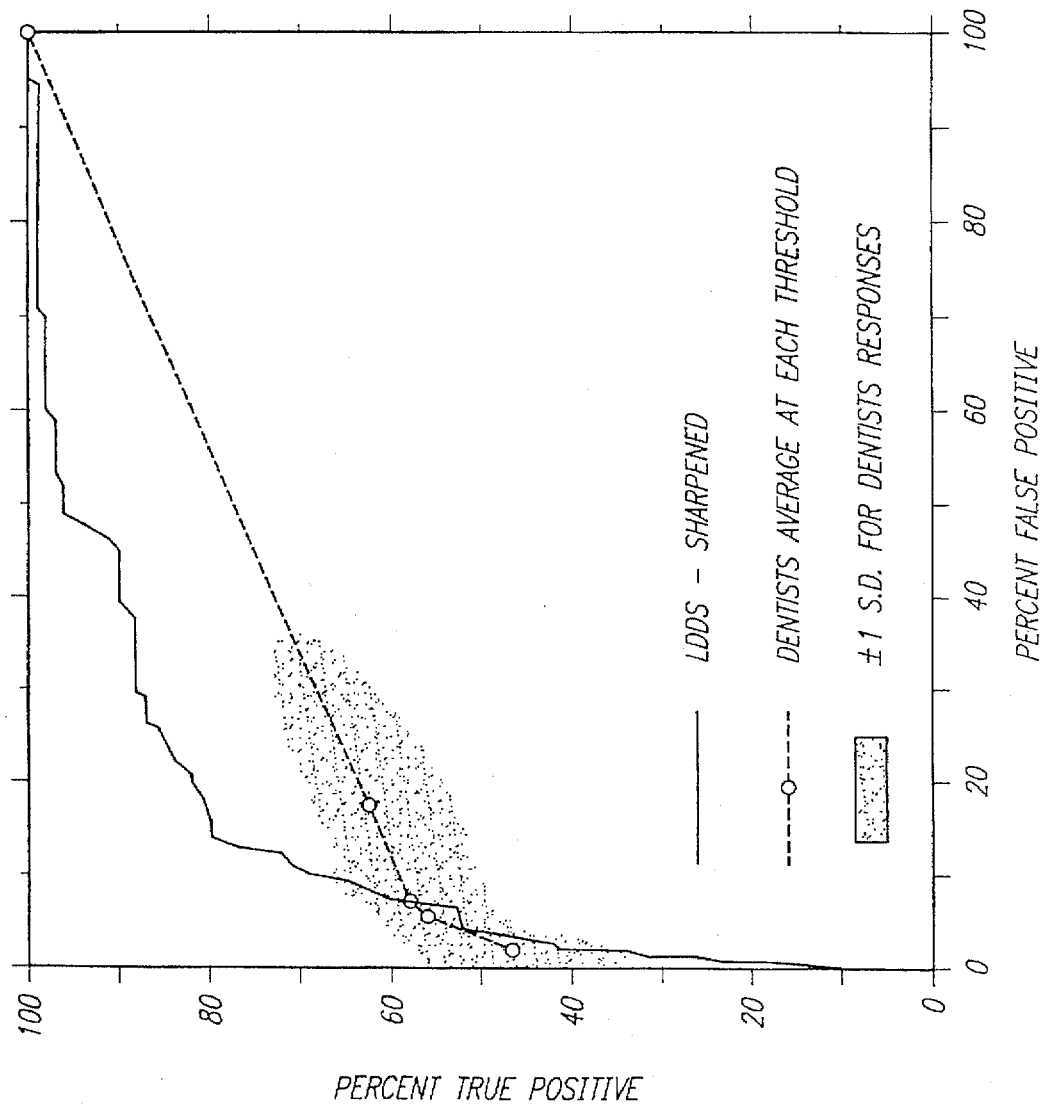
FIG. 6 compares the performance of the quantitative dental caries detection system for finding dentinal lesions in molars using sharpened direct digital images with the performance of dentists and additionally illustrates plus and minus one standard deviation about the mean of the dentists' responses.

FIG. 6 compares the performance of the quantitative dental caries detection system 20 on sharpened direct digital images of molars with the performance of dentists and, as in FIG. 5, additionally illustrates plus and minus one standard deviation about the mean of the dentists' responses.

Figure 7:
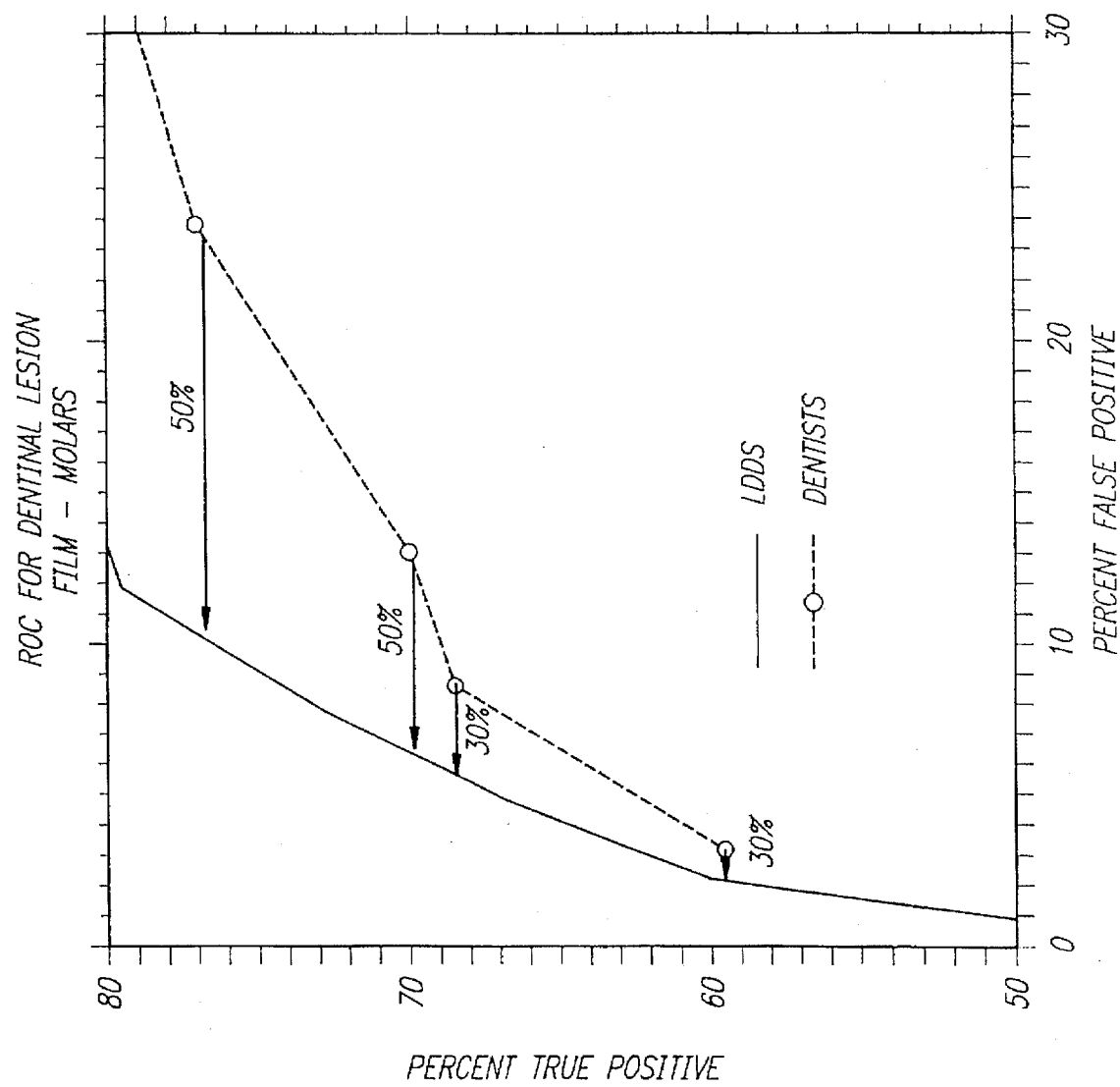
FIG. 7 is an enlarged view of a portion of the plot shown in FIG. 5 and provides a quantitative comparison between the detection system of the present invention and the mean response of dentists.

FIG. 7 is an enlarged view of a portion of the plot shown in FIG. 5 and provides a quantitative comparison between the detection system 20 and the mean response of dentists in the more clinically relevant lower end of the ROC. The 30–50% reduction in the false positive identification rate at the lower end of the ROC demonstrates the diagnostic advantage provided by the detection system 20 because it is in this area of the ROC curve that difficult decisions are presented to the dentist. Notwithstanding the scattered individual responses of the dentists (FIG. 5), the quantitative dental caries detection system 20 outperforms the average response of the tested dentists in the majority of cases and is consistent in its evaluation, unlike dentists' responses. In fact, the detection system 20 generates a single, consistent response when run in "automatic mode"(i.e., all tissue boundaries determined by the detection system 20). Consistent responses are provided by the detection system 20 when used correctly, keying in on the correct anatomical tissue landmarks.

Figure 8:
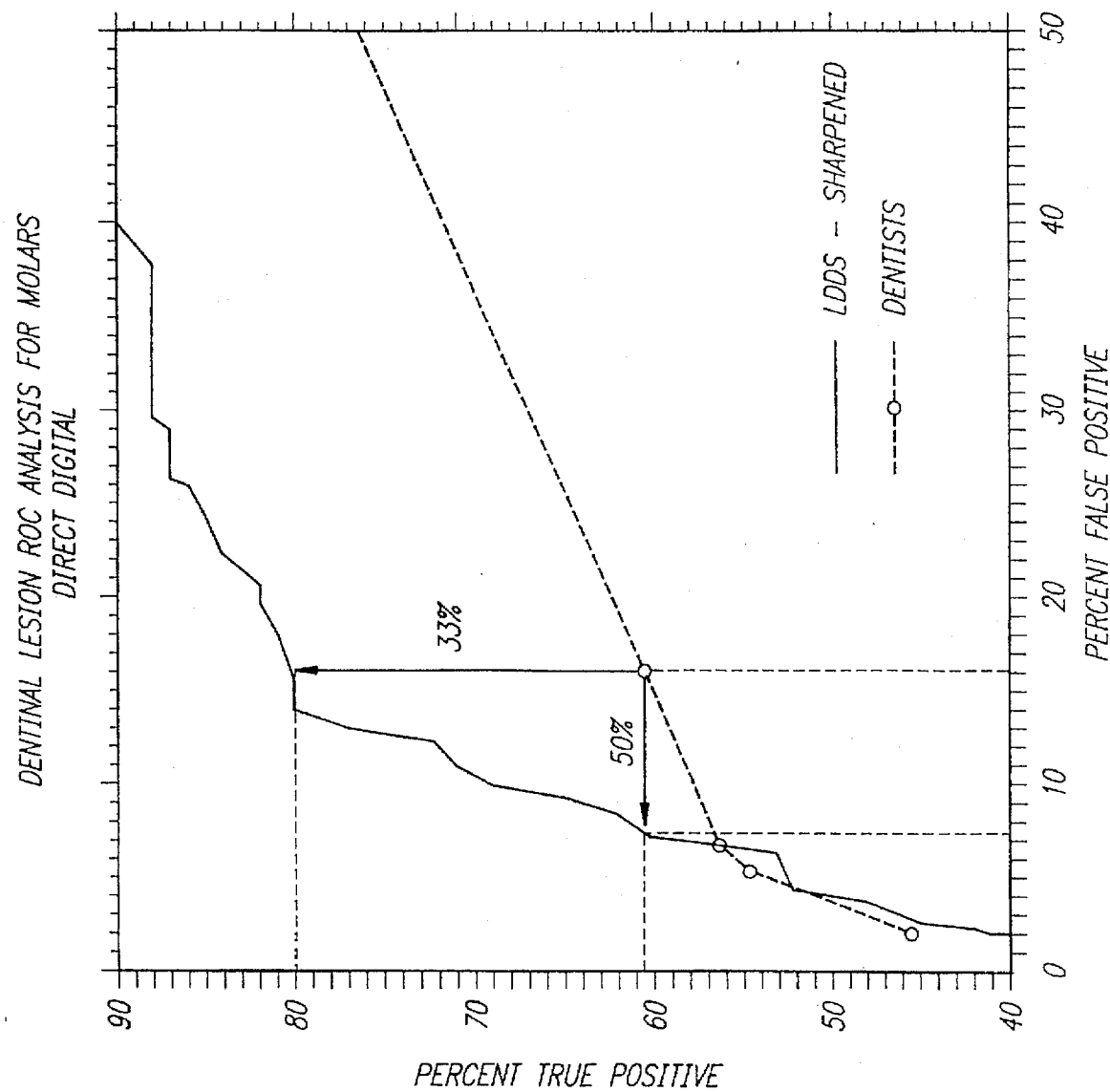
FIG. 8 is an enlarged view of a portion of the plot shown in FIG. 6 and provides a quantitative comparison between the detection system of the present invention and the mean response of dentists.
Figure 9:
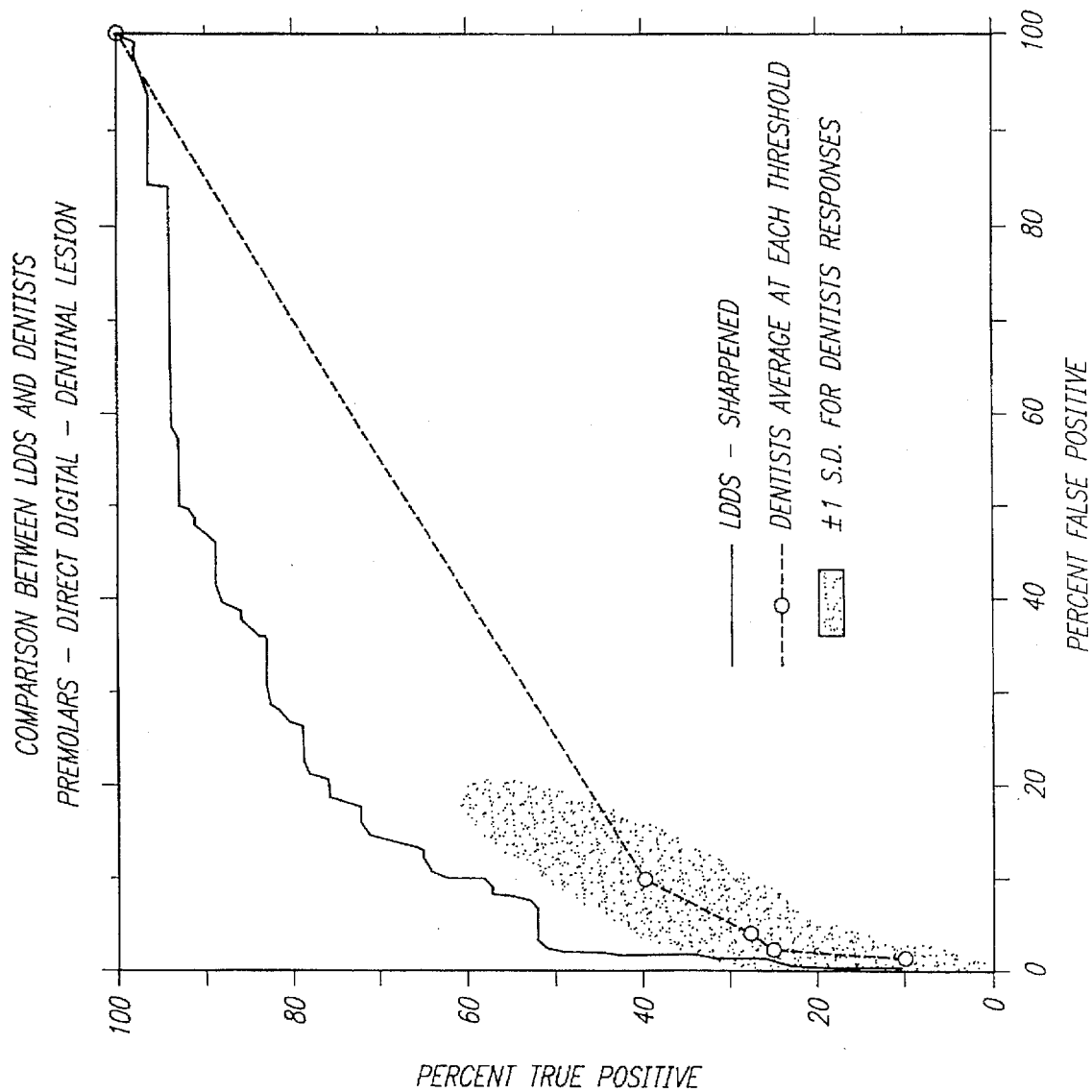
FIG. 9 compares the performance of the quantitative dental caries detection system for finding dentinal lesions in FIG. 10 compares the performance of the quantitative dental caries detection system for finding dentinal lesions in canines with the performance of dentists and additionally illustrates plus and minus one standard deviation about the mean of the dentists' responses.
Figure 10:
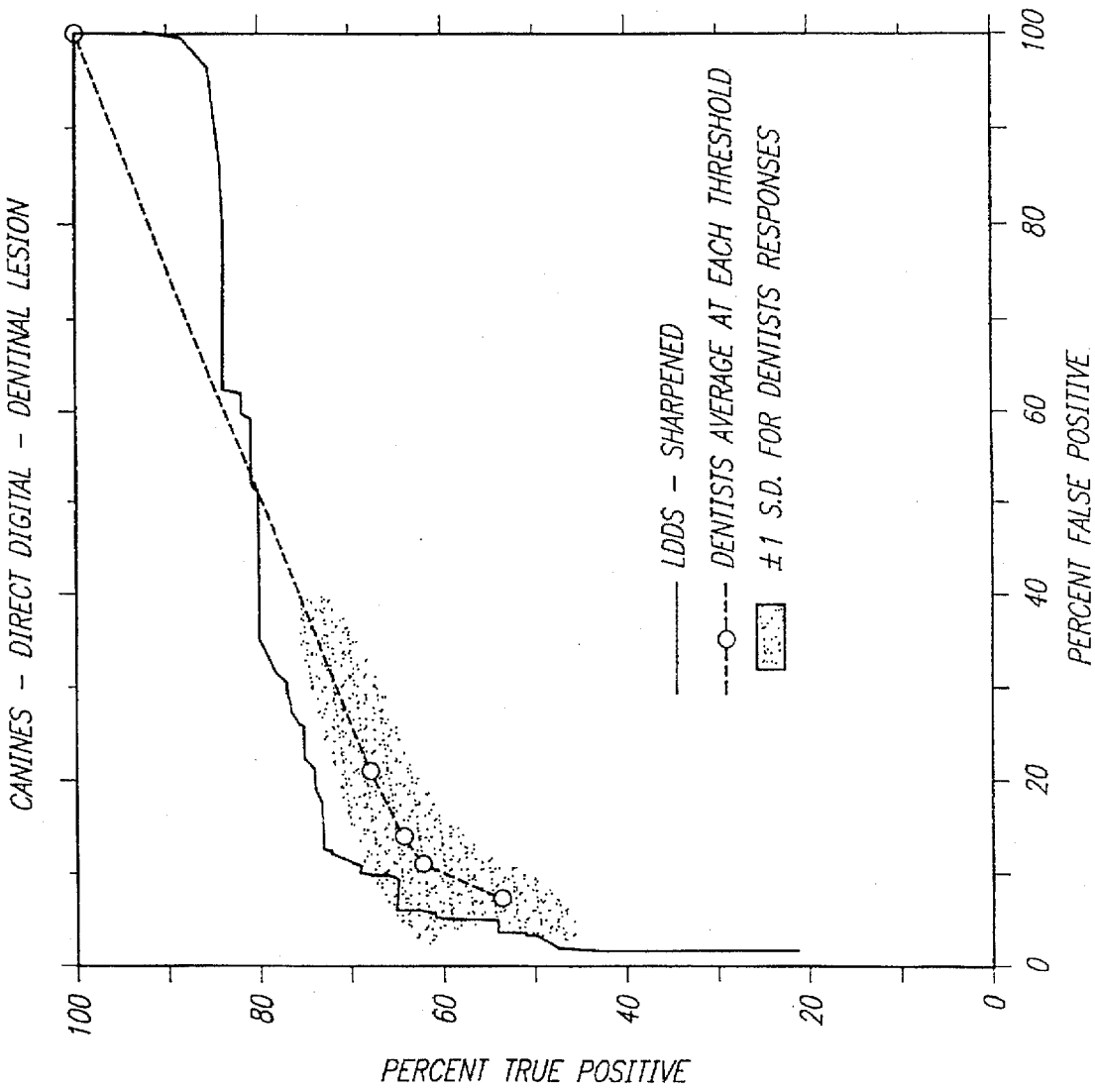
Figure 11:
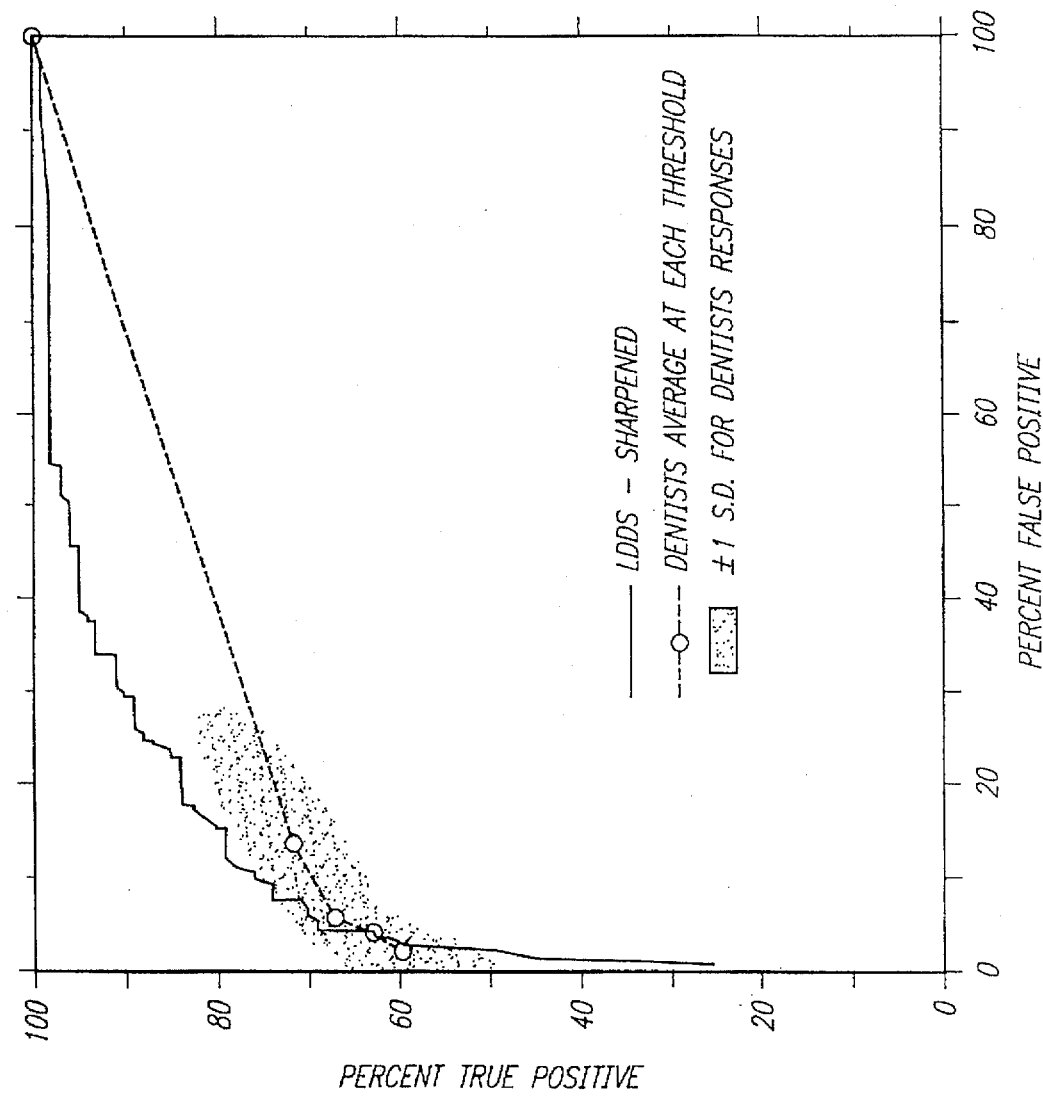
FIG. 11 compares the performance of the quantitative dental caries detection system for finding dentinal lesions in incisors with the performance of dentists and additionally illustrates plus and minus one standard deviation about the mean of the dentists' responses.

FIG. 8 is an enlarged view of a portion of the plot shown in FIG. 6 and provides a quantitative comparison between the detection system 20 and the mean response of dentists. As with film, the detection system 20 reduces the false positive identification rate for sharpened direct digital images of molars at the critical lower end of the ROC thereby reducing the unnecessary treatment of teeth. More specifically, FIG. 8 illustrates that dentists identify approximately 62% of all dentinal lesions at a false positive rate of approximately 16% . An LDDS interpretation of the same enhanced direct digital radiographs identifies the same percentage of lesions while reducing the false positive rate to approximately 7% (a 50% reduction). Alternately, an LDDS interpretation of the same enhanced direct digital image maintains the same false positive rate as dentists while increasing the rate of lesion identification to 80% (a 33% increase).

In a fashion similar to FIG. 6, FIGS. 9, 10 and 11 compare the performance of the quantitative dental caries detection system 20 on sharpened direct digital images of premolars, canines and incisors respectively, with the performance of dentists, additionally illustrating plus and minus one standard deviation about the mean of the dentist's responses. As with molars, LDDS equals or exceeds the performance of dentists on direct digital images of premolars, canines and incisors.

In conclusion, it is to be understood that the foregoing detailed description and the accompanying drawings illustrate the principles of the invention. However, various changes and modifications may be employed without departing from the spirit and scope of the invention. Thus, by way of example and not of limitation, the system and method of the present invention may be employed to detect lesions in other types of tissues besides teeth. For example, mammograms, chest x-rays, tissue characterization and cell characterization and other applications are contemplated. Accordingly, the present invention is not limited to the specific form shown in the drawings and described in detail hereinabove.

What is claimed is:

1. A system for the digital detection of dental lesions or caries comprising:
   a digitized x-ray image of teeth, said image having variable image intensities;
   means for identifying the outer surface of a tooth in a predetermined area, and for identifying the interface between the enamel and the dentine;
   means for identifying significant changes in intensity along successive spaced lines extending substantially parallel to the tooth surface and substantially parallel to the interface between the enamel and the dentine within the enamel, and within the dentine adjacent to and parallel to the interface and for processing portions of said image to identify features within the enamel and the dentine;

means for processing said image to generate statistics pertaining to said features and to identify best linear alignments of dark features in each of said tissues, said feature statistics including:
an enamel penetration depth;
an enamel feature magnitude;
an enamel feature alignment error;
a dentine feature magnitude;
a dentinal feature alignment error; and
a degree of colinearity between enamel features and dentinal features;

means for processing said feature statistics and for comparing the variations in intensity with stored data relating to known dental lesions or caries, and for determining by such comparison probabilities of dental lesions being present and extents of such lesions; and means for printing out the variations in intensity along said successive spaced lines, showing the presence or absence of dental lesions in the enamel and/or dentine, and the extents of such lesions if they are present.

2. A system for the digital detection of dental lesions or caries comprising:
a digitized x-ray image of teeth, said image having variable image intensities;
means for identifying the outer surface of a tooth in a predetermined area, and for identifying the interface between the enamel and the dentine;
means for identifying significant changes in intensity along successive spaced lines extending substantially parallel to the tooth surface and substantially parallel to the interface between the enamel and the dentine within the enamel, and within the dentine adjacent to and parallel to the interface, and for processing portions of aid image to identify features within the enamel and the dentine;
means for processing said image to generate statistics pertaining to aid features and to identify best linear alignments of dark feature in each of said tissues,.said feature statistics including:
an enamel penetration depth;
an enamel feature magnitude;
an enamel feature alignment error;
a dentine feature magnitude;
a dentinal feature alignment error; and
a degree of colinearity between enamel features and dentinal features; and
means for displaying the intensity along said successive spaced lines, showing the presence or absence of dental lesions in the enamel and/or dentine, and the extents of such lesions if they are present.

3. A method for the digital detection of dental lesions or caries comprising:
obtaining digitized x-ray images of teeth, said images having variable image intensities;
identifying the outer surface of a tooth in a predetermined area in said digited images and identifying the interface between the enamel and the dentine;
identifying significant changes in intensity along successive spaced lines extending substantially parallel to the tooth surface and substantially parallel to the interface between the enamel and the dentine within the enamel, and within the dentine adjacent to and parallel to the interface, and processing portions of said image to identify features within the enamel and the dentine;

processing said image to generate statistics pertaining to said features and to identify best linear alignments of dark feature in each of said issues, said feature statistics including:
an enamel penetration depth;
an enamel feature magnitude;
an enamel feature alignment error;
a dentine feature magnitude;
a dentinal feature alignment error; and
a degree of colinearity between enamel features and dentinal features;

processing said feature statistics and comparing the variations in intensity with stored data relating to known dental lesions or caries, and determining by such comparison probabilities of dental lesions being present and extents of such lesions; and displaying the variations in intensity along said successive spaced lines, showing the presence or absence of dental lesions in the enamel and/or dentine, and the extents of such lesions if they are present.

4. A method for quantifying a probability of lesions existing in tissues, comprising the steps of:
(a) processing an image of at least two adjacent tissues to determine a junction between said tissues and an outer boundary of an least one of said tissues, thereby establishing segments of said image;
(b) processing portions of said image within each said segment to identify features within said tissues;
(c) processing said image to generate statistics pertaining to said features and to identify best linear alignments of dark features in each of said tissues, said feature statistics including:
an enamel penetration depth;
an enamel feature magnitude;
enamel feature alignment error;
a dentine feature magnitudes;
a dentinal feature alignment error; and
a degree of colinearity between enamel features and dentinal features; and
(d) processing said feature statistics to determine probabilities of said features being lesions.

5. The method for quantifying a probability of lesions existing in tissues of claim 4 wherein said segmentation processing step comprises:
employing a gradient method search to determine said outer boundary, said segmentation processing step (a) being controlled by segmentation parameters which are established in consideration of an optimization of said gradient method search.

6. The method for quantifying a probability of lesions existing in tissues of claim 4 wherein:
said image has a degree of sharpness; and
said segmentation processing step (a) is controlled by segmentation parameters which are established in consideration of said degree of sharpness of said image being processed.

7. The method for quantifying a probability of lesions existing in tissues of claim 4 wherein:
said portions of said image of said feature extraction processing step (b) are determined in consideration of said junction and said outer boundary.

8. The method for quantifying a probability of lesions existing in tissues of claim 4 wherein said portions of said image of said feature extraction processing step (b) comprise families of traces within said outer boundary.

9. The method for quantifying a probability of lesions existing in tissues of claim 4 wherein said portions of said image of said feature extraction processing step (b) comprise traces substantially parallel to said junction and said outer boundary.

10. A method for quantifying a probability of lesions existing in tissues, comprising the steps of:

(a) processing an image of at least two adjacent histologically different tissues to determine a junction between said tissues and an outer boundary of at least one of said tissues, thereby establishing segments of said image;

(b) processing portions of said image within each said segment to identify features within said tissues, said portions of said image of said feature extraction processing step (b) comprising traces substantially parallel to said junction and said outer boundary, said feature extraction processing step (b) further comprising the steps of:

determining pixel intensities along said traces;

determining variations of said intensities along said traces; and processing said intensity variations to identify locations and magnitudes of said features along said traces;

(c) processing said image to generate statistics pertaining to said features and to identify best linear alignments of dark features in each of said tissues, said feature statistics including:

an enamel penetration depth;
an enamel feature magnitude;
an enamel feature alignment error;
a dentine feature magnitude;
a dentinal feature alignment error; and
a degree of colinearity between enamel features and dentinal features;

(d) training a neural network classifier with feature statistics derived from images of tissues similar to said at least two adjacent histologically different tissues but with known histologically verified lesions; and (e) processing said feature statistics of said step (c) with said neural network classifier to determine probabilities of said features being lesions.

11. A method for quantifying a probability of lesions existing in tissues, comprising the steps of:

(a) processing an image of at least two adjacent tissues to establish segments of said image;

(b) processing portions of said image within each said segment to identify features within said tissues, said feature extraction processing step (b) further comprising:

determining pixel intensities within said portions;

determining variations o said intensities within said portions; and processing said intensity variations to identify locations and magnitudes of said features within said portions;

(c) processing said image to generate statistics pertaining to said features and to identify best linear alignments of dark features in each of said tissues, and said feature statistics including:

an enamel penetration depth;
an enamel feature magnitude;
an enamel feature alignment error;
a dentine feature magnitude;
a dentinal feature alignment error; and
a degree of colinearity between enamel features and dentinal features; and (d) processing said feature statistics to determine probabilities of said features being lesions.

12. The method for quantifying a probability of lesions existing in tissues of claim 11 wherein said feature statistics processing step (c) comprises:

performing linear regressions on said portions of said image to generate least squares errors which are weighted by said magnitudes of said features.

13. The method for quantifying a probability of lesions existing in tissues of claim 11 wherein said best linear alignments of said feature statistics processing step (c) are determined differently as between said segments.

14. A method for quantifying a probability of lesions existing in tissues, comprising the steps of:

(a) processing an image of at least two adjacent tissues including enamel and dentine to establish segments of said image;

(b) processing portions of said image within each said segment to identify features within said tissues;

(c) processing said image to generate statistics pertaining to said features and to identify best linear alignments of dark features in each of said tissues, said feature statistics including:

an enamel penetration depth;
an enamel feature magnitude;
an enamel feature alignment error;
a dentine feature magnitude;
a dentinal feature alignment error; and
a degree of colinearity between enamel features and dentinal features;

(d) training a neural network classifier with feature statistics derived from images of tissues similar to said at least two adjacent histologically different tissues but with known histologically verified lesions; and (e) processing said feature statistics of said step (c) with said neural network classifier to determine probabilities of said features being lesions.

15. A method for quantifying a probability of lesions existing in tissues, comprising the steps of:

(a) processing an image of at least two adjacent histologically different tissues to establish segments of said image;

(b) processing portions of said image within each said segment to identify features within said tissues;

(c) processing said image to generate statistics pertaining to said features and to identify best linear alignments of dark features in each of said tissues, and said feature statistics including:

an enamel penetration depth;
an enamel feature magnitude;
an enamel feature alignment error;
a dentine feature magnitude;
a dentinal feature alignment error; and
a degree of colinearity between enamel features and dentinal features;

(d) training a neural network classifier with feature statistics derived from images of tissues similar to said at least two adjacent histologically different tissues but with known histologically verified lesions; and (e) processing said feature statistics of said step (c) with said neural network classifier to determine probabilities of said features being lesions, said neural network classifier comprising a fully connected, three layer, feed-forward network employing trained network weights to determine said probabilities of said features being lesions.

16. A method for quantifying a probability of lesions existing in tissues, comprising the steps of:
   (a) processing an image of at least two adjacent histologically different tissues to establish segments of said image;
   (b) processing portions of said image within each said segment to identify features within said tissues;
   (c) processing said image to generate statistics pertaining to said features and to identify best linear alignments of dark features in each of said tissues, and said feature statistics including:
      an enamel penetration depth;
      an enamel feature magnitude;
      an enamel feature alignment error;
      a dentine feature magnitude;
      a dentinal feature alignment error; and
      a degree of colinearity between enamel features and dentinal features; and
   (d) processing said feature statistics to determine probabilities of said features being lesions.

17. A system for quantifying a probability of lesions existing in tissues, comprising:
   a memory device embodying a computer executable program for:
   (a) processing an image of at least two adjacent histologically different tissues to establish segments of said image;
   (b) processing portions of said image within each said segment to identify features within said tissues;
   (c) processing said image to generate statistics pertaining to said features and to identify best linear alignments of dark features in each of said tissues and said feature statistics including:
      an enamel penetration depth;
      an enamel feature magnitude;
      an enamel feature alignment error;
      a dentine feature magnitude;
      a dentinal feature alignment error; and
      a degree of colinearity between enamel features and dentinal features; and
   (d) processing said feature statistics to determine probabilities of said features being lesions.

18. The system for quantifying a probability of lesions existing in tissues of claim 17, further comprising:
   a printer for printing visible indicia of said probabilities.

* * * * *